United States Patent [19]
Dam

[11] Patent Number: 5,507,178
[45] Date of Patent: Apr. 16, 1996

[54] LIQUID PRESENCE AND IDENTIFICATION SENSOR

[75] Inventor: Naim Dam, Muttontown, N.Y.

[73] Assignee: Cosense, Inc, Hauppauge, N.Y.

[21] Appl. No.: 337,329

[22] Filed: Nov. 9, 1994

[51] Int. Cl.$^6$ .......................... G01F 23/26; G01N 15/02
[52] U.S. Cl. .................. 73/61.490; 73/304; 73/290 R; 340/603; 340/618; 181/140; 181/124
[58] Field of Search .................. 73/61.49, 304 C; 340/618, 603, 620; 181/124

[56] References Cited

U.S. PATENT DOCUMENTS

| | | | |
|---|---|---|---|
| 4,733,560 | 3/1988 | Dam | 73/304 C |
| 4,782,698 | 11/1988 | Wilson | 73/304 C |
| 4,788,488 | 11/1988 | Kramer et al. | 324/61 R |
| 4,820,973 | 4/1989 | Alvarez | 324/61 R |
| 4,882,928 | 11/1989 | Lane Jr. et al. | 73/19 |
| 5,043,707 | 8/1991 | Heinze | 340/618 |
| 5,049,878 | 9/1991 | Stern | 340/870.4 |
| 5,051,921 | 9/1991 | Paglione | 364/509 |
| 5,123,275 | 6/1992 | Daoud et al. | 73/19.03 |
| 5,287,086 | 2/1994 | Gibb | 340/618 |
| 5,392,638 | 2/1995 | Kawahara | 73/61.49 |

FOREIGN PATENT DOCUMENTS 5575645  6/1980  Japan .................. 73/61.49

*Primary Examiner*—Hezron E. Williams
*Assistant Examiner*—J. David Wiggins

[57] ABSTRACT

A sensor for determining both the presence of a liquid in a container or conduit, and identifying its type has a sensor housing body containing both a pair of piezoelectric elements used as the transmitter and receiver of ultrasonic waves directed across a gap therebetween in an ultrasonic liquid presence detecting circuit and a pair of electrodes exposed to any of such liquid in the gap used in a circuit for identifying the liquid type. The liquid identification circuit is either of the capacitance type, which produces a variable amplitude output signal depending on the type of liquid in the gap between the two electrodes, or operates to measure the difference in response time between pulses applied to each of the electrodes with one serving as a reference.

17 Claims, 4 Drawing Sheets

LIQUID PRESENCE AND IDENTIFICATION SENSOR

BACKGROUND OF THE INVENTION

Ultrasonic sensors are well known for the detection of the presence of a liquid. One such type of sensor includes a housing to be placed in the location where liquid presence is to be detected which holds a transmitting and receiving element, such as a piezoelectric crystal, separated by an air gap. An amplifier is in the path between the two crystal elements. When there is no liquid present in the gap, the sensor produces no signal. When liquid is present in the gap, the amplifier gain becomes greater than one, i.e. the circuit oscillates, and an output signal is produced to indicate the presence of the liquid.

It is also desired in some cases to determine the type of liquid, for example, discriminate between the presence of water, gasoline, oil or a combination thereof, so that appropriate action can be taken. A typical application is in a leak detector used in connection with double hull storage tanks at a gasoline station to determine if there is liquid leaking between the two walls of the tank and the type of liquid leaking.

Brief Description of the Invention

The present invention relates to a sensor in which the elements necessary for both liquid presence and liquid type identification are all contained in a single housing. In accordance with the invention, the housing includes the transmitting and receiving piezoelectric elements separated by an air gap. Also included within the housing are electrodes which are part of circuit for identifying the type of liquid and producing a corresponding output when liquid presence is detected in the air gap by the ultrasonic portion of the sensor. One type of circuit is of the capacitance type which produces a signal whose amplitude is indicative of the type of liquid present in the air gap.

In a preferred embodiment of the invention, a liquid identification circuit is provided which operates on a pulse width measurement basis between pulses from a reference electrode and pulses from an active electrode which senses the liquid. This type of circuit corrects for possible errors which can occur due to dimensional variations in the sensor housing and other factors.

BRIEF DESCRIPTION OF THE DRAWINGS

Other objects and advantages of the present invention will become more apparent upon reference to the following specification and annexed drawings in which.

DETAILED DESCRIPTION OF THE INVENTION

Figure 1:
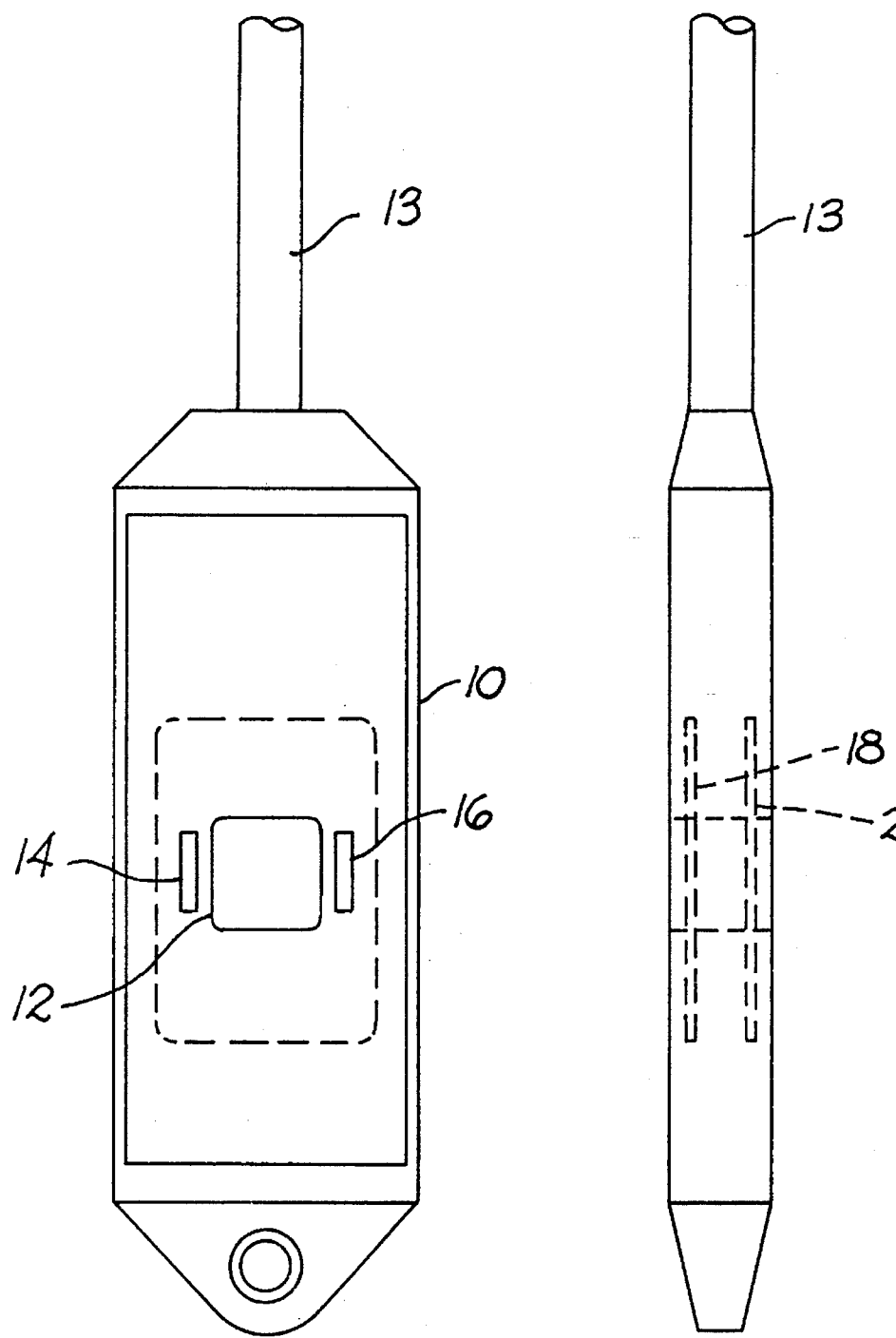
FIGS. 1A and 1B are plan and side views of the sensor housing.

FIG. 1 shows a form of the sensor housing body 10 which is of generally rectangular shape. The housing body can be of any suitable material, such as epoxy resin, which is an electrically insulating material, KYNAR plastic, etc. Typical dimensions are a length of about 4.25" long by 1.50" wide by 0.43" thick. Any suitable dimensions can be used, as required for a particular application.

The housing 10 has an open air gap section 12. While a generally square shape is shown, the air gap section can be of any desired shape such as rectangular or round. The gap 12 is shown illustratively in the mid-part of the housing, but it can be located at any part, such as near one end.

A cable 13 extends from the housing. The cable has the necessary leads for input voltages to operate electronic components within the housing and output signals which convey information of the operation of the sensor to a remote device or system (not shown) used for monitoring the vessel with which the sensor operates.

Embedded in the housing 10 on opposing sides of the air gap section 12 in the thickness dimension of the housing are ultrasonic transmit and receive crystals 14 and 16. These can be of any suitable piezoelectric material, such as PZT. Also embedded in housing 10 generally parallel to its upper and lower faces are a pair of metallic electrodes 18, 20 which are part of a capacitance sensing circuit. At least a part of the capacitance electrodes 18, 20 extend into the gap 12. For example, the electrodes 18, 20 can be of annular shape with only the inner peripheral portion of each electrode extending into the air gap to oppose each other to form the plates of a capacitor and so that liquid can still enter the gap. As seen in FIG. 1, the crystals 14, 16 are disposed between the electrodes 18, 20. Any other suitable arrangement can be used for mounting the crystals 14, 16 and the electrodes 18, 20.

Also embedded within the housing 10 is the electronic circuitry for the sensor. If desired, the electronics can be located remote from the housing and the operating signals for the sensors conveyed via leads in cable 13. The electronics includes an oscillating loop type ultrasonic liquid presence detecting circuit. This has an amplifier 22, which can be a fairly high gain RF or video amplifier, whose input is connected to crystal element 16 through a matching network 24 which is formed of components such as capacitors and coils (not shown) to match the impedance of element 16.

The output of amplifier 22 is connected to the input of an automatic gain control circuit 26 which makes the output of the ultrasonic circuit of relatively constant amplitude. An envelope detector 28 is connected to the output of the gain control 26 and its output is connected to a signal converter 30 which converts the signal level to a form which is usable by the remote monitoring system, e.g. the conventional 4–20 ma signal range as is used by many monitoring systems. The other ultrasonic crystal element 14 is connected to the gain control circuit 26 through another matching network 24.

In operation of the ultrasonic circuit, when there is no liquid in the housing gap 12 between the two crystal elements 14, 16, the amplifier loop is quiescent since ultrasonic energy cannot be transmitted through the air across the gap between elements 14, 16. When liquid is present in the gap, ultrasonic energy at a frequency determined by the characteristics of the crystal elements 14, 16 is transmitted across the gap between the elements and the loop is completed. The gain of amplifier 22 is greater than one and the circuit will begin to oscillate. This is detected by envelope detector 28 and an output signal is produced which actuates the signal converter 30 to send a signal indicating the presence of a liquid sensed over cable 13 to the remote monitor.

The ultrasonic portion of the sensor has a self test switch 32. This is actually located at the remote location and via leads in cable 13 effects a short circuit across, i.e. connects, the crystal elements 14, 16 to simulate the presence of a liquid in gap 12. This permits the ultrasonic portion of the sensor to be tested.

The liquid discrimination portion of the sensor includes a clock pulse generator 40 operating at a suitable frequency, such as 20 Khz. The clock pulses, which are either square or rectangular, are applied to a driver-amplifier 42 which sends these pulses to one of the capacitor plates 20. The input of an amplifier 43 is connected to the other capacitor plate 18 and the output of amplifier 43 connected to the input of a detector 46.

In operation, when there is no liquid in the gap 12 the amplifier 43 and detector 46 are set to produce a fixed reference output amplitude signal in response to pulses from the driver 42 traveling across the gap 12. That is, there is air as the dielectric in the path between the capacitor electrodes 18, 20. When liquid in present in gap 12 the dielectric constant of the signal transmission path between electrodes 18, 20 through the liquid changes.

The amplitude of the signal at the input of amplifier 43 depends on the type of liquid in the gap and its dielectric constant. The variable amplitude output signal from amplifier 43 is detected by detector 46 and converted into a variable current signal by convertor 30 whose output level identifies the liquid. Detector 46 can be of the stepped type to produce discrete level output signals in response to amplitude ranges of input signals. For example, a signal level at the output of detector 46 in response to water being present between electrodes 18, 20 produces a current level signal of about 20 ma, the presence of oil and/or gasoline about 10 ma, and the absence of liquid (presence of air) is designated by about 4 ma.

A self-test circuit for the liquid type discriminating portion of the sensor is formed by a logic circuit 53 and driver 55 connected between the clock 40 and a switch 57 which is across the electrodes 18, 20. This is usually actuated at the same time that the ultrasonic circuit self-test switch is actuated from a remote location.

Figure 2:
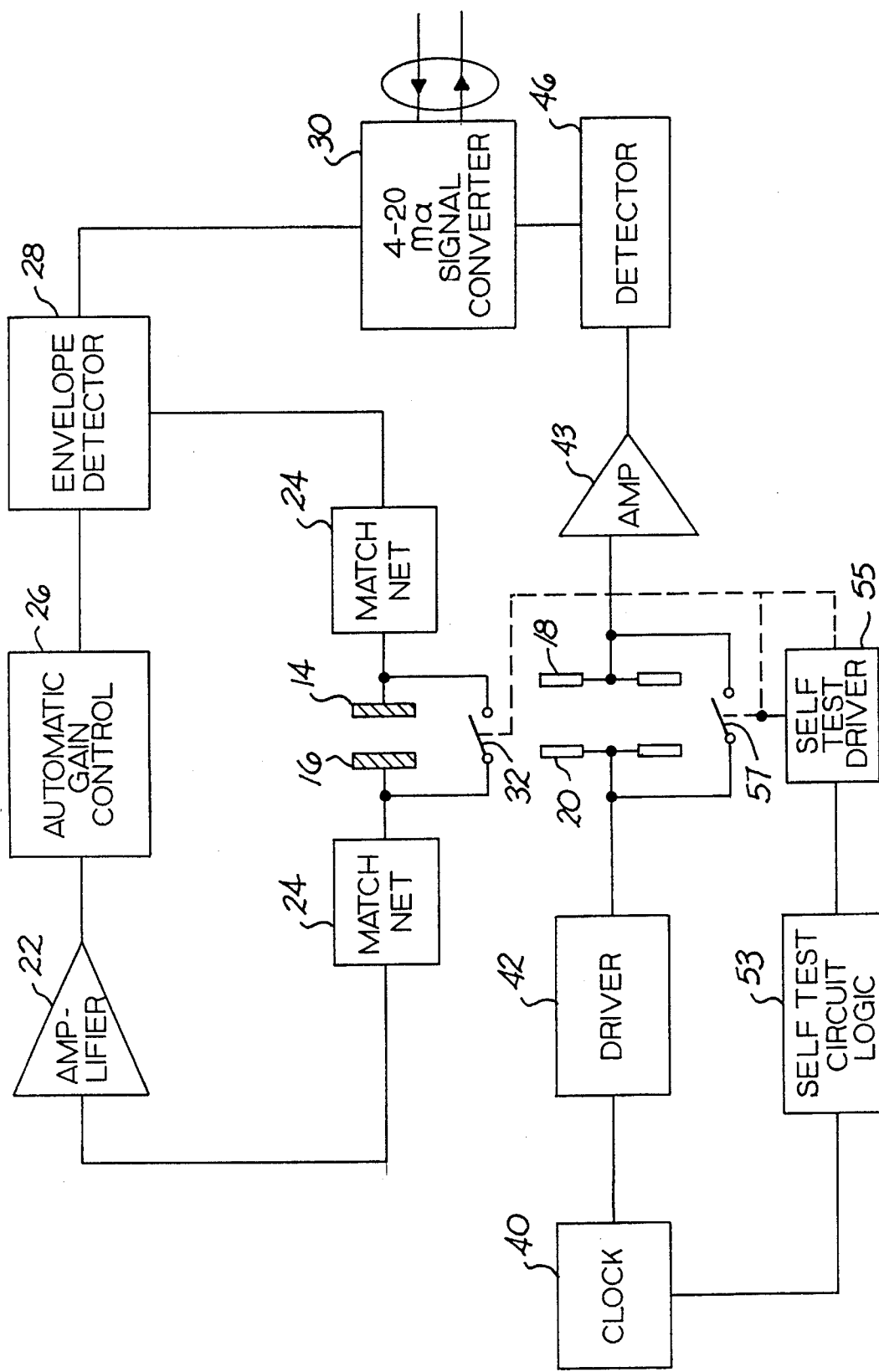
FIG. 2 is a schematic block diagram of one embodiment of the invention.
Figure 3:
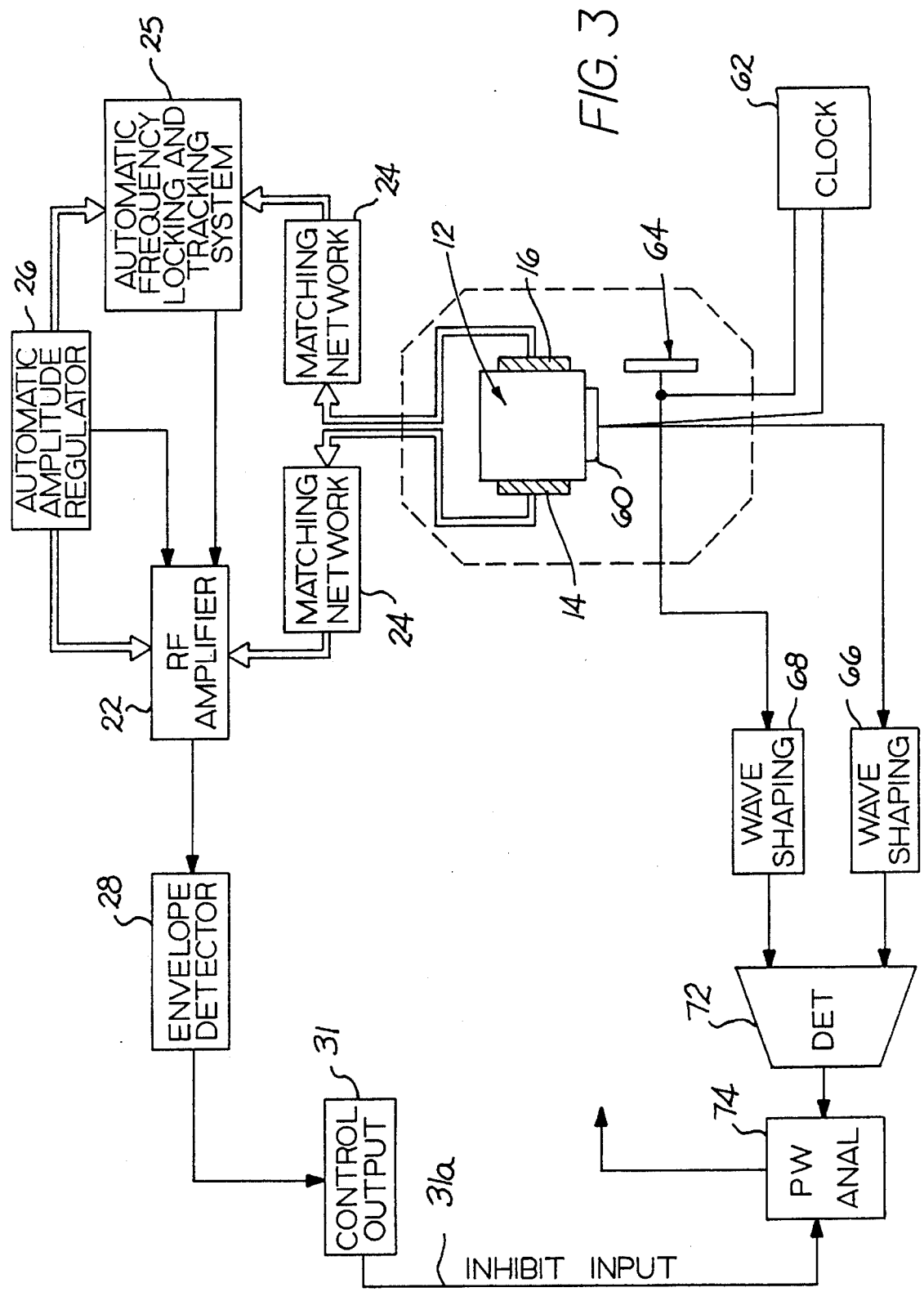
FIG. 3 is a schematic diagram of another embodiment of the invention.
Figure 4:
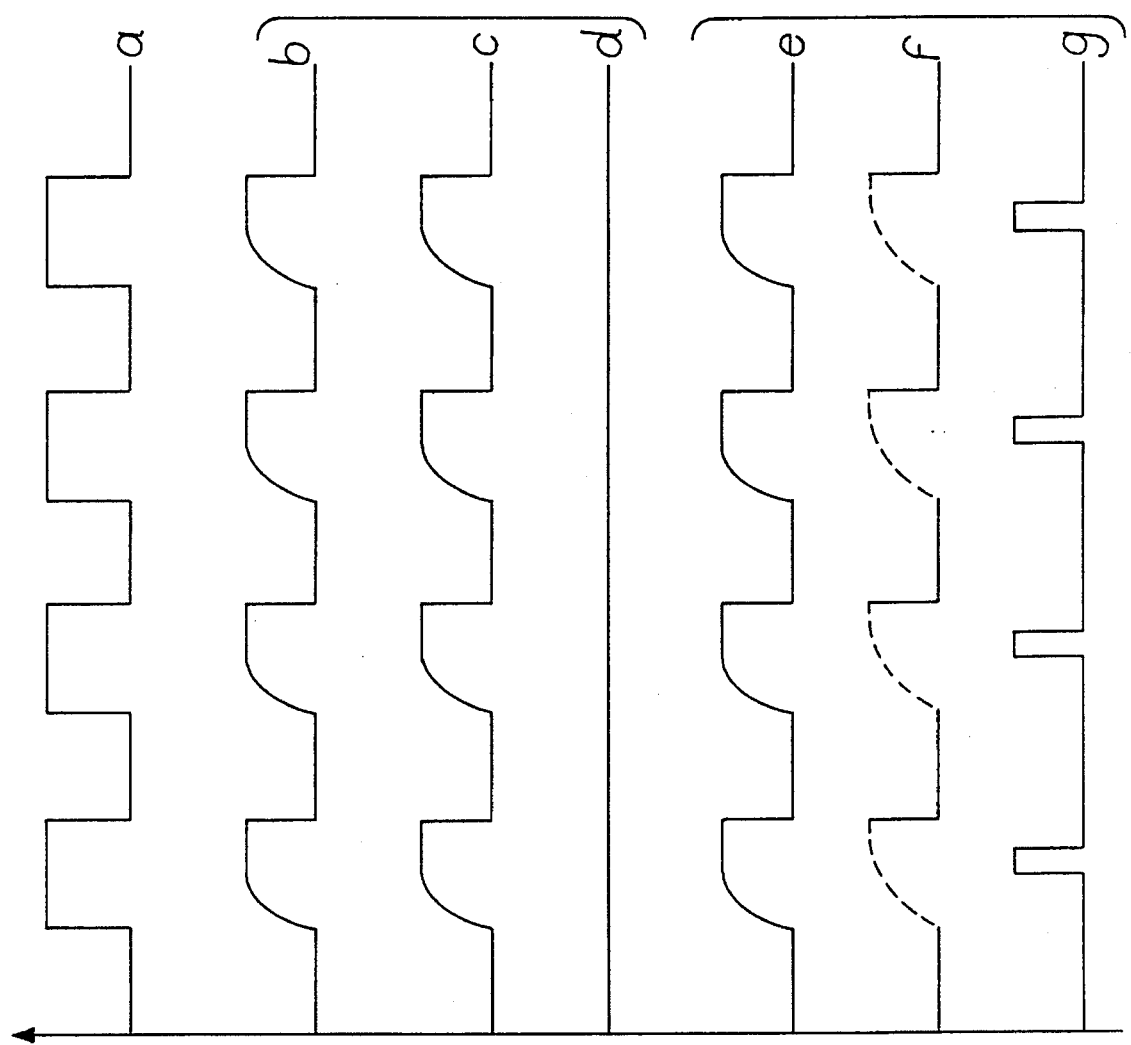
FIG. 4 shows waveforms present at various points of the circuit of FIG. 3.

FIGS. 3 and 4 show an embodiment which improves the operation of the circuit of FIG. 2, for example to overcome sensor response variations due to dimensional differences and materials of the housing body. FIG. 3 uses the same reference numerals used in FIGS. 1 and 2 for the same components.

In FIG. 3, the ultrasonic portion of the circuit is essentially the same as in FIG. 2. This circuit also includes an automatic frequency tracking and locking circuit 25 which locks the frequency of the circuit at or near the resonance frequency when it begins to oscillate. The oscillation frequency otherwise possibly can shift due to changes in liquid characteristics, such as viscosity, temperature, etc. The output of the envelope detector 28 feeds a control output circuit 31 which produces an enable signal on line 31a to permit the liquid identification portion of the circuit to produce an output.

For the liquid identification circuit there is an active electrode 60 and a reference electrode 64. These can have the same configuration and be located in the same positions as shown in FIG. 1. The reference electrode 64 is connected to electronic circuit ground. A clock pulse generator 62 applies pulses to each of the electrodes 60 and 64 for transmission into the gap 12. The gap 12 can be looked at as serving as a terminating impedance for the pulses from the electrodes 60 and 64. This impedance changes depending upon the status of the gap that is, the presence or absence of liquid in the gap and the type of liquid.

The electrodes 60 and 64 are respectively connected to the input of a wave shaping circuit 66, 68 which rounds the trailing edge portion of the waveforms and leaves a part of the top edge flat. The outputs of the wave shapers 66, 68 are connected to a response time measurement detector 70.

FIG. 4 shows the waveforms produced during the operation of the liquid identification circuit. Line a shows the clock pulses from generator 62. Lines b, c and d illustrate the situation when there is no liquid in the gap 12. In this case the active electrode 60 and reference electrode 64 each see the same terminating impedance, that is, the air gap, so the input to the respective wave shapers 66 and 68 and their respective outputs, as shown on lines b and c are the same. As can be seen from lines b and c, the wave shapers 66, 68 rounds about one half of the width of the trailing part of each of the pulses. Since the signals on lines b and c applied to and coming out of the wave shapers 66, 68 are the same, the phase detector 72 has no output as shown on line d.

Lines e, f and g of FIG. 4 illustrate the situation where there is liquid present in gap 12. Here the output of the wave shaper 68 which is connected to the reference electrode 64 is the same as in line b since it is connected to circuit ground. However, the pulse output of wave shaper 66 connected to active electrode 60, whose termination is the liquid in the gap between the two electrodes which changes since the liquid present in the gap 12 provides a different terminating impedance. This is shown on line f. This changes the response time for the output of the wave shaper 66 to reach a flat top level condition. The presence of different types of liquids in gap 12 produces different response time curves and different shapes for the output pulses of wave shaper 66. That is, depending upon the type of the liquid present in gap 12 the waveform at the output of wave shaper varies with respect to the length of the flat top portion due to the resonse time variation. The response time comparison between the two waveforms takes place based upon the lengths of the flat portion of the two waves being compared.

The detector 72 produces pulses, as shown on line g, of a width corresponding to the difference caused by the change in shape of the pulses at the output of active electrode wave shaper 66 as compared to the output of reference electrode wave shaper 68. The width of the pulses on line g varies depending upon the type of liquid in gap 12 into which active electrode 60 operates. For example, the presence of water causes a repetition pulse output of one width, gasoline another and so forth.

The output of response time detector 72 is applied to a pulse width analyzer 74. This circuit operates to produce an output corresponding to the width of the response time input pulses. Pulse width analyzer 74 is enabled to operate when there is a signal from the output of the ultrasonic sensor via control output 31. That is, the liquid identification circuit can only produce an output when the ultrasonic circuit has confirmed the presence of a liquid.

The output of pulse width analyzer 74 is preferably in electrical current form, as is conventional in the process control field with which the sensor of the invention finds an intended use. For example, a current output of 4 ma indicates the absence of a liquid in gap 12, 10 ma oil or gasoline and 20 ma water.

The sensor of the invention has a number of advantages. It combines liquid presence detection as well as liquid identification integrally into a unitary housing body. The material of the sensor body housing can be selected to be compatible with most hydrocarbon products such as oil, gasoline, diesel fuel, transmission fluid, etc. The small size of the housing body permits its use in small spaces and it can be placed in vessels having small openings.

The ultrasonic circuitry is independent of the color, density or viscosity of the liquid. No calibration is required.

I claim:

1. A sensor for detecting the presence of a liquid within an open or closed container or conduit and for identifying the type of liquid comprising;

a sensor housing body of an electrically insulating material having a gap, said body to be placed in said container or conduit and liquid therein to enter said gap for detection of liquid presence and identification of the type of liquid in said gap;

said sensor having liquid presence sensing means and liquid type identification means including;

a pair of ultrasonic elements mounted in said body at respective spaced locations at least partially opposing each other and separated around said gap with one element serving as a transmitter of ultrasonic energy and the other as a receiver of the energy transmitted by said one element, circuit means connected to said elements for producing an indication of the presence of a liquid in said gap of said body upon energy being transmitted between said elements through liquid present in said gap, liquid type identification means including;

a pair of electrodes mounted on said body in spaced relationship, at least one of said electrodes positioned relative to said gap to have an electrical signal transmitting relationship with liquid in the gap;

electrical pulse generating means connected to said at least one electrode, the electrical pulses received by said at least one electrode from said pulse generating means being transmitted to the liquid in said gap, and identification means connected to said at least one electrode and responsive to the electrical pulses received thereby to determine the type of liquid in said gap.

2. The sensor as in claim 1 wherein said liquid presence means and said liquid type identification means are integral in said housing body.

3. The sensor as in claim 1 wherein said liquid type identification means includes a pair of spaced electrodes adjacent said gap to be in electrical signal transmitting relationship with liquid in said gap and said determining means responds to the dielectric constant property of liquid in said gap between said pair of electrodes.

4. The sensor as in claim 3 wherein said determining means produces a variable amplitude level signal as the sensor electrical output corresponding to liquid type identification.

5. The sensor as in claim 1 wherein said liquid type identification means includes a pair of electrodes mounted on said body each of which electrodes receives pulses from said pulse generator, one of said electrodes being set at a reference potential point, and said determining means includes means for measuring the difference in the response time between the pulses supplied to and returned from said pair of electrodes.

6. The sensor as in claim 5 wherein said difference measuring means includes means for shaping the form of each of the pulses returned from each electrode of said pair of electrodes.

7. The sensor as in claim 5 wherein said measuring means produces a variable width pulse dependent upon the type of liquid in said gap.

8. The sensor as in claim 7 further comprising means for producing a signal identifying the type of liquid present in said gap in response to the width of the variable width pulse.

9. The sensor as in claim 3 wherein said pair of ultrasonic elements and said pair of electrodes are mounted on said body generally transverse to each other.

10. The sensor as in claim 5 wherein said pair of ultrasonic elements and said pair of electrodes are mounted on said body generally transverse to each other.

11. The sensor as in claim 3 wherein each said electrode of said pair of electrodes has a portion embedded in said body and a portion extending into said gap.

12. The sensor as in claim 5 wherein each said electrode of said pair of electrodes has a portion embedded in said body and a portion extending into said gap.

13. The sensor as in claim 1 wherein said body has length, width and thickness dimensions, said gap being through the thickness dimension of said body and being surrounded at least in part by said body.

14. The sensor of claim 13 wherein said at least one electrode is generally parallel to a cross-section of said body containing its length and width dimensions and said at least one electrode surrounds at least a portion of said gap.

15. The sensor as in claim 3 wherein said body has length, width and thickness dimensions, said gap being through the thickness dimension of said body and being surrounded by said body, said pair of spaced electrodes being generally parallel to a cross-section of said body containing its length and width dimensions and each electrode of said pair surrounding at least a portion of said gap.

16. A sensor for detecting the presence of a liquid within an open or closed container or conduit comprising;

a sensor housing body of an electrically insulating material having a gap for admitting any liquid present therein, said body having length, width and thickness dimensions, said gap being a passage through the thickness dimension of said body with said passage being entirely surrounded by said body, said body to be placed in said container or conduit and liquid therein to enter said gap for liquid presence detection;

liquid presence determination means in said housing body including a pair of ultrasonic elements mounted integrally in said body at respective spaced locations at least partially opposing each other and separated around adjacent sides of said gap adjacent sides of with one element serving as a transmitter of ultrasonic energy and the other element serving as a receiver of the ultrasonic energy transmitted by said one element, and circuit means connected to said elements for producing an indication of the presence of a liquid in said gap upon energy being transmitted between said elements through liquid present in said gap.

17. The sensor of claim 16 wherein said gap has at least two opposing sides and each of said ultrasonic elements is mounted adjacent a respective one of said sides opposing the other ultrasonic element.

* * * * *